United States Patent [19]
Del Grande et al.

[11] Patent Number: 5,444,241
[45] Date of Patent: Aug. 22, 1995

[54] EMISSIVITY CORRECTED INFRARED METHOD FOR IMAGING ANOMALOUS STRUCTURAL HEAT FLOWS

[75] Inventors: Nancy K. Del Grande, San Leandro; Philip F. Durbin, Livermore; Kenneth W. Dolan, Livermore; Dwight E. Perkins, Livermore, all of Calif.

[73] Assignee: The Regents of the University of California, Oakland, Calif.

[21] Appl. No.: 130,486

[22] Filed: Oct. 1, 1993

[51] Int. Cl.⁶ .................................. G01N 21/71
[52] U.S. Cl. .................... 250/253; 250/339.06; 250/339.14; 250/341.6
[58] Field of Search .............. 250/339.14, 339.11, 250/339.06, 341, 340, 253, 341.6

[56] References Cited

U.S. PATENT DOCUMENTS

4,005,289  1/1977  Del Grande .................. 250/253
5,111,048  5/1992  Devitt et al. ................. 250/342

OTHER PUBLICATIONS

Nancy K. Del Grande—Dual-Band Infrared Imaging Applications: Locating Buried Minefields, Mapping Sea Ice, and Inspecting Aging Aircraft—(Sep. 1992)—Lawrence Livermore National Laboratory UCRL -J-C-111214 preprint.

N. K. Del Grande et al—Dynamic Thermal Tomography for Nondestructive Inspection of Aging Aircraft—Lawrence Livermore National Laboratory (undated).

N. K. Del Grande et al—Three-dimensional dynamic thermal imaging of structural flaws by duel-band infrared computed tomography—Lawrence Livermore National Laboratory (undated).

P. F. Durban et al—Dual-Band Infrared Thermography for Quantitive Nondestructive evaluation—Lawrence Livermore National Laboratory (undated).

*Primary Examiner*—Constantine Hannaher
*Attorney, Agent, or Firm*—Henry P. Sartorio; John P. Wooldridge

[57] ABSTRACT

A method for detecting flaws in structures using dual band infrared radiation. Heat is applied to the structure being evaluated. The structure is scanned for two different wavelengths and data obtained in the form of images. Images are used to remove clutter to form a corrected image. The existence and nature of a flaw is determined by investigating a variety of features.

27 Claims, 1 Drawing Sheet

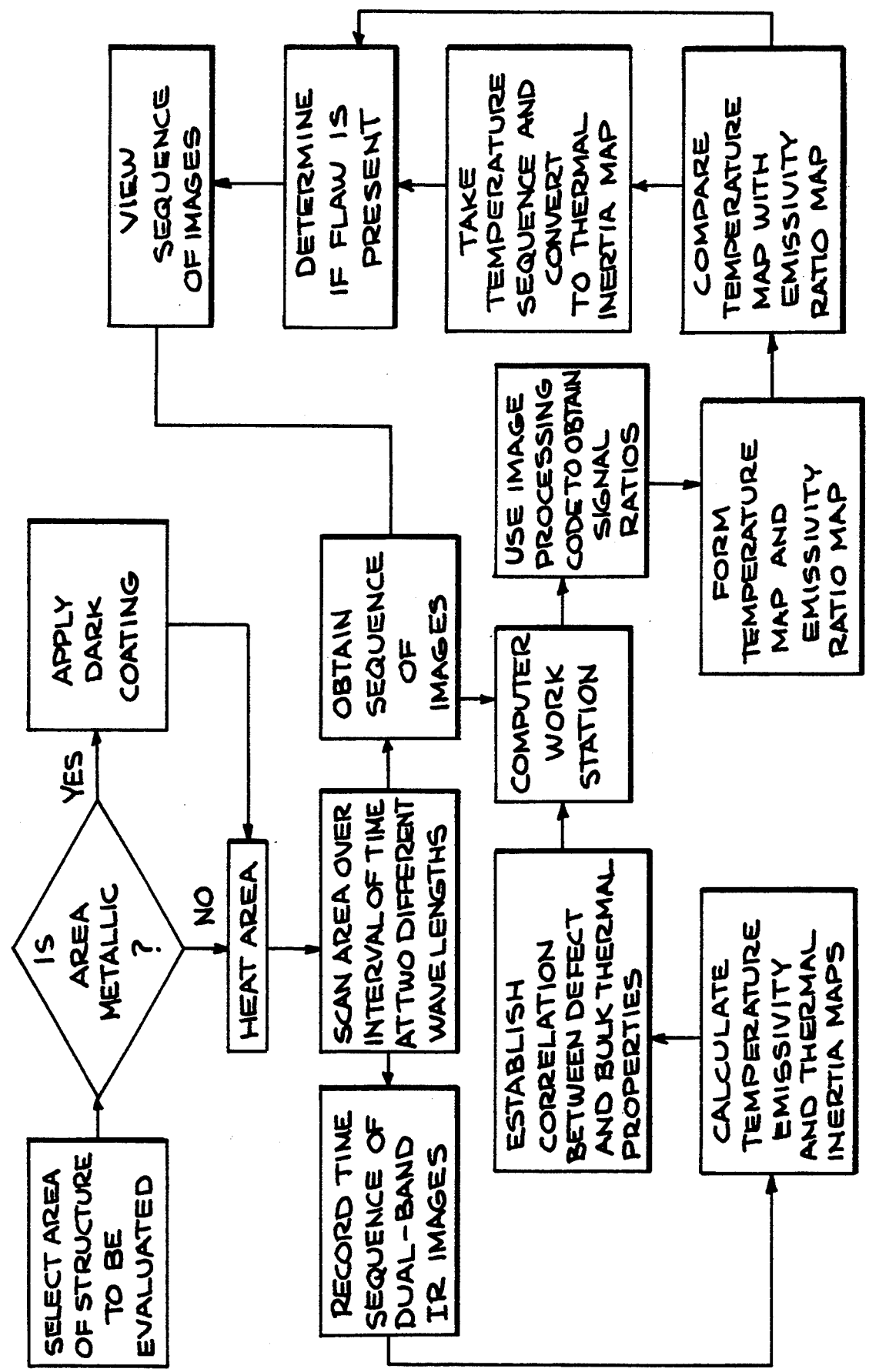

EMISSIVITY CORRECTED INFRARED METHOD FOR IMAGING ANOMALOUS STRUCTURAL HEAT FLOWS

ORIGIN OF THE INVENTION

The United States Government has rights in this invention pursuant to Contract No. W-7405-ENG-48 between the United States Department of Energy and the University of California for the operation of Lawrence Livermore National Laboratory.

BACKGROUND OF INVENTION

Dual Band Infrared (DBIR) Imaging has numerous advantages over conventional thermal imaging which utilizes only a single band. Conventional thermal imaging is difficult to interpret. It yields imprecise information that is insensitive to the subtle heat flow anomalies produced by subsurface flaws. These conventional imaging techniques fail to distinguish between surface emissivity clutter and true temperatures. In addition, emissivity-related noise, typically 1° C. or 2° C., cannot be removed using a single passive thermal IR band even when used in conjunction with another active laser reflectance IR band.

DBIR imaging has most recently been applied to the detection of buried land mines by exploiting temperature differences between the mine site and the surrounding soil. U.S. Pat. No. 4,005,289 describes this method, its contents which are incorporated herein by reference.

Lap joints were studied in the present invention, because a lap joint that had the adhesion bond removed (disbond) played a significant role in causing damage to the Aloha Aircraft fuselage on the aged Boeing 737 jetliner which produced loss of life several years ago.

SUMMARY OF THE INVENTION

The present invention is directed to detecting a flaw in a man-made structure using infared computed tomography by heating the structure with a heat source, scanning an area of the structure with at least two different wavelengths of radiation to thus obtain a sequence of images, and determining whether a flaw is present in the structure from the sequence of images.

Scanning an area of a structure during a predetermined interval of time produces images composed of signals. A signal is the portion of an image at a point in time that corresponds to desired information. In the present invention, the desired information includes heat flow through a structural area under observation. Thus, signals may correspond to surface temperature data and surface emissivity data of the structure at a plurality of points in time. By contrast, noise is that portion of the image produced by clutter and other undesired data.

The invention may further include eliminating noise generated by clutter from the sequence of images to form a corrected image. Noise arises in part from apparent temperature effects. Apparent temperature is composed of a combination of surface and emissivity effects. For example, a greybody that has a temperature of 20 degrees C., may appear to have a temperature of 18 degrees C. because radiation is not absorbed or emitted at 100%. That is, some infrared radiation is reflected and thereby results in an inaccurate temperature known as apparent temperature. This inaccuracy is corrected by using two different wavelength bands in accordance with the present invention. Noise can be eliminated by separating surface apparent temperature data from spatially varying surface emissivity data to thereby obtain corrected temperature values at scanned points of the structure. The separation of surface temperature data from spatially-varying surface emissivity data can also be achieved by using a temperature ratio equation to obtain a temperature map. The separation of surface temperature data from spatially-varying surface emissivity data can be achieved by using an emissivity ratio equation to obtain an emissivity ratio map. The temperature map may then be compared with the emissivity-ratio map to observe heat flow anomalies in order to determine whether a flaw exists.

The present invention is also directed to a method for detecting a flaw in a structure using a combination of infrared, x-ray and acoustic sensor images.

The present invention is further directed to detecting a flaw in a structure using infrared computed tomography by scanning the structure with at least two different wavelengths; obtaining a sequence of images; eliminating noise associated with surface emissivity produced by clutter associated with a man-made structure from said sequence to form a corrected image; and determining from the corrected image whether or not a flaw exists.

When an area of a structure is scanned, an image representing the temperature and emissivity feature is produced. An area of a structure can be scanned using a long wavelength band (LWB) ranging from 8–12 micrometers and a short wavelength band (SWB) ranging from 3–5 micrometers. Scanning in these ranges of wavelengths is preferred because a typical greybody surface will have nearly the same emissivity at one wavelength between the 3–5 micrometers, as it does at a second wavelength, between 8–12 micrometers. However, one of ordinary skill in the art could select other ranges and still produce acceptable results. The minimum number of detectors used during scanning is preferably at least equal to the number of scanned wavelengths.

An additional embodiment of the invention involves determining the size of a flaw in a man-made structure using infrared computed tomography wherein: an area of the structure is scanned using at least two different infrared (IR) wavelengths of radiation; a sequence of images is obtained; noise associated with non-terrestrial surface emissivity clutter is eliminated from said sequence to form a corrected image; and the size of the flaw is determined from the corrected image.

The present invention may be used to evaluate a wide variety of structures such as aircraft, pipes, electronic components, bridges and highways. In addition, any type of infrastructure may be evaluated with the present invention.

BRIEF DESCRIPTION OF THE DRAWING

The FIGURE is a block diagram that illustrates the steps of the present invention.

DETAILED DESCRIPTION OF THE INVENTION

A man-made structure having a flaw such as a crack or a delamination is characterized by heat transferring through the flaw at a different rate than it does through flawless regions of the structure. The resulting differences in surface temperature are referred to herein as heat flow anomalies.

Heat flow anomalies may be detected by remotely sensed radiation. The remotely sensed radiation is preferably corrected for the effects of surface emissivity, meteorology, structural topography, and surface material differences, including thermal inertia prior to obtaining any quantitative temperature measurement suitable for detecting structural flaws.

Cumulative extraneous effects (e.g. noise produced by clutter) that can mask temperature anomalies are often an order of magnitude greater than the desired anomalous component. Appropriate corrections are therefore preferably made before useful interpretations can be made from surface temperature data of structures. Atmospheric corrections for radiant temperature measurements is preferably made both for the absorption and emission in the intervening air path (between the surface and the scanner) and for the sky radiation reflecting off the structure. The basic steps in isolating anomalous temperatures of structural flaws include (1) heating the area of interest, (2) measuring the true surface temperature over the area of interest at a given time, (3) obtaining a color-coded image corrected for noise, and (4) determining whether a flaw is present in the area under evaluation.

In accordance with a preferred embodiment of the invention, the first step in measuring the true temperature over a given structural area is to record the radiant temperature over this area using an infrared scanner capable of sensing emitted energy having at least two different wavelengths. After the radiant temperature data is recorded, it is calibrated and the calibrated radiant temperature data is corrected for: (a) variations in surface emissivity, (b) absorption and remission in the atmospheric column between the surface and the scanner, and (c) sky radiation reflected from the surface of the structure.

Planck's law states that radiation emitted by a source can be related to its temperature. More precisely, Planck's law states that the radiant emittance of a surface is proportional to emissivity times absolute temperature to the power of (50/wavelength in microns).

A power law thermal model provides the physical rationale for ratioing narrow IR bands involving calculating mathematical ratios using signals with equations derived from Planck's law to produce signal ratios. These signal ratios are insensitive to the natural surface emissivity and provide enhanced thermal responsivity. The derivation of this model is given in the Appendix of Geophysics, Vol. 41, No. 6, pp. 1335–1336 (December 1976). In accordance with the preferred embodiment, this model is used to determine signal ratios which are in turn used to remove surface emissivity noise.

The emissivity of a structure is highly variable from one area to another. However the ratio of signals at two or more wavelengths can be used to obtain highly precise surface-temperature measurements that depend very little upon emissivity variations. For example, temperature differences as small as 0.2° C. can be obtained by using the present invention. Thus, it is preferred to determine this ratio in the method of the present invention.

At wavelengths where the radiation has the same spectral slope as a blackbody source, i.e. an object that absorbs all radiation, the emissivity ratio variations are very small. Thus, in a preferred aspect of the invention, quantitative temperature measurements are made using signal ratios that are calibrated against a standard blackbody source.

A typical greybody surface is an object that absorbs about 95–99% of all radiation and thus has an emissivity of less than 1. If a structure is a greybody, its respective temperatures will look alike at wavelengths of 5 micrometers and 10 micrometers.

Where the surveyed structure behaves in true greybody fashion, no matter what area is scanned, the ratio of emissivity at one wavelength divided by the emissivity at a second wavelength ($\epsilon_{\lambda 1}/\epsilon_{\lambda 2}$) is constant. The ratio of two signals at differing wavelengths can then be calibrated and the blackbody temperature obtained. In a preferred aspect of the present invention, $\lambda_1 = 5$ μm and $\lambda_2 = 10$ μm, respectively, because these are the common wavelengths that are recorded by present-day scanners.

Because the heat flow anomaly is difficult to accurately measure, corrections are preferably made to accurately associate the thermal anomaly with a structural flaw. Furthermore, measured surface temperatures of a particular structure can be inaccurate because of an emissivity factor (noise) generated by clutter. Clutter may include dirt, ink, dents, tape, markings, oil, grease, sealants, paint stripper, exposed metal, uneven paint and roughness variations. The emissivity factor produced by noise relates to the ability of clutter surfaces to emit radiant energy compared to that of a black body at the same temperature and with the same area. Thus, a black body is an ideal structure that absorbs all radiation without reflection.

The present invention provides a method for detecting a flaw in a man-made structure using infrared computed tomography which masks the effect of clutter. The structure is analyzed using visual, photographic, x-ray and acoustic sensor techniques to characterize the defect. Specifically, the method includes heating the structure with a passive or active heat source, and preferably when the structure is metallic and applying a dark coating to the structure prior to heating it. The heat source comprises a flashlamp, a laser, conduction means, convection means or other radiant heating means. An area of said structure is then scanned simultaneously at two or more different wavelengths of radiation to produce a time sequence of images. The time sequence of images is processed into signal ratios that are used to eliminate clutter. The removal of pixels generated by clutter thus minimizes noise and thereby produces a corrected image, the time behavior of which can be used to determine whether a flaw exists in the structure.

Obtaining a temperature versus time history is important to determine the size, shape, depth, type and location of a flaw. Despite the elimination of clutter, images cannot be interpreted very easily without also studying the time history of infrared image ratios. Other informative maps may be generated based on the temperature-time history.

Suitable structures that may be examined using the present method include structures having plastic, metallic, ceramic or composite surfaces. In a preferred embodiment, aircraft, infrastructure, electronic components and pipes may be inspected and evaluated for corrosion or other flaws which would hamper their performance.

In the case of an aircraft, the detected flaw may include corrosion, delamination, disbonding, an indentation or any other surface or subsurface inhomogeneity. The structure to be analyzed in accordance with the present invention is subjected to a heat source either before or during the scanning step. The heat source may be selected from a laser, a flashlamp, other radiant heating means, conduction means or convection means. In addition, the heat source may be simply natural sunlight. Preferably, the heat source is an intense flashlamp. Suitable flashlamps include Norman (4000 joule) and Balcor (6000 joule) lamps. Although the structure under evaluation is preferably pulse-heated immediately before scanning, it can also be heated while scanning is taking place.

Images from scanning are displayed on a screen and have colors that correspond to temperature. The frames that record each picture element (pixel) are each acquired at a unique time, so no two pixels in a frame are recorded at exactly the same time. The images in the sequence are obtained at intervals of between 0.5 ms to 100 ms, over a period of time ranging from 2 seconds to 8 minutes.

Further in accordance with the preferred embodiment, the corrected temperature data is used to generate corrected temperature maps. Corrected temperature maps are color-coded images that show color patterns of conducted heat generated by objects which heat and cool at different rates relative to the surrounding materials. These patterns are distinguished from the patterns produced by outside surfaces of the structure.

The interpretation of the images is improved by removing the clutter and thus increasing the signal to noise ratio. As a result, corrected images are formed, thereby facilitating the detection of heat flow anomalies associated with flaws.

In accordance with the present invention, dual-band signal ratios and signal differences which vary in time as the heated target cools can be used to distinguish temperature from surface emissivity noise effects on the resulting thermal imagery collected at wavelengths centered near 5 and 10 micrometers.

Equations 1–4 can be used to determine signal ratios which may be used to remove surface emissivity noise. This is done by enhancing surface temperature contrast, and thereby more easily removing pixels which represent emissivity noise. A temperature map based on equation 2 has enhanced contrast. In addition, a correction is preferably made for the effects of sky radiation reflecting off the structure (assuming that this is a problem). This correction is proportional to $(1-\epsilon)/\epsilon$ times the recorded temperature minus the sky temperature, where $\epsilon$ is the surface emissivity. Of course, this correction is not necessary for measurements taken indoors.

The basis for associating certain digitized signals with clutter is based on the relationships set forth in equations 1–4 below:

Infrared signals vary as a function of the surface emissivity and the surface's absolute temperature as follows:

$$I_\lambda \sim e_\lambda T^{50/\lambda} \qquad (1)$$

where $I_\lambda$ is the intensity at a given wavelength, $e_\lambda$ is emissivity at that wavelength, T is temperature in Kelvin and $\lambda$ is the wavelength in micrometers.

The temperature by itself is obtained by computing the ratio $$R = \frac{I_5}{I_{10}} = \frac{e_5 T^{50/5}}{e_{10} T^{50/10}} = \frac{e_5}{e_{10}} T^5, \qquad (2)$$

For a greybody, $e_5 = e_{10}$ and $R \sim T^5$.

The emissivity ratio is obtained by computing $$\frac{(I_{10})^2}{I_5} = \frac{(e_{10})^2 (T^5)^2}{e_5 T^{10}} = \frac{(e_{10})^2}{e_5} \qquad (3)$$

This ratio is sensitive primarily to surface objects which have very different emissivities at 5 and 10 micrometers (most metal surfaces). The DBIR ratios are then computed to obtain enhanced temperature contrast ($T^5$) and emissivity-ratio (E-ratio) maps:

$$(T/T_{AV})^5 = (S/S_{av})/(L/L_{av}) \text{ and}$$
$$\text{E-ratio} = (L/L_{av})^2/(S/S_{av}) \qquad (4)$$

where S is the short wavelength intensity (e.g., $I_5$), $S_{av}$ is the average value of the pixels in S, L is the long wavelength intensity (e.g., $I_{10}$) and $L_{av}$ is the average value of the pixels in L.

EXAMPLES

Example 1

The method was applied to a lap joint taken from an aircraft. The lap joint was formed from a section composed of two aluminum panels overlapping at their edges and fastened together with a joint. In this case, the panels are also attached at the joint with an epoxy glue bond.

The time history of surface temperature difference patterns at the epoxy-glue disbond site of a flash-heated lap joint was captured. The lap joint was scanned with two passive IR scanners, an InSb scanner for the short wavelength and a Hg-Cd-Te scanner for the long wavelength.

The scans were taken every 40 ms from 0 to 8 seconds after the heat flash at two different wavelengths. These scans were used to produce a sequence of images. Two images were concurrently taken at a wavelength between 3–5 micrometers and another wavelength between 8–12 micrometers. An Agema 880 DBIR camera system and Burst Recording Unit were used to record the digitized SWB and LWB infrared images. The digitized images were input to a Silicon Graphics Inc. workstation. By ratioing the two different images, surface temperature patterns from weak heat flow anomalies at the disbond site were located. The emissivity mask from surface paint or roughness variations was removed. Thus, the disbond site was located and relevant data was isolated from the clutter.

Example 2

Aircraft panels from a Boeing 737 were flashheated. Synchronized DBIR images were recorded every 40 ms, from onset to 8 seconds after the heat flash. To increase thermal gain from the flash lamps, the aluminum panels were painted with Crayola black (water soluble) paint.

Image processing software codes such as VIEW (a software package available from Lawrence Livermore National Laboratory of Livermore, Calif.) provided enhanced temperature contrast maps, emissivity-ratio maps, thermal inertia maps, dynamic thermal response curves and other information to characterize subtle heat flow anomalies from hidden structural defects.

Example 3

Pipes above ground level were analyzed for corrosion and other defects. The area of interest on said pipes was scanned at two different wavelengths, while the pipes were exposed to natural sunlight. Data from the sequence of images obtained were processed by image processing software into surface temperature ratios and emissivity ratios. Emissivity ratios corresponded to surface roughness effects generated by the outside surface of the pipes from sky reflection off the pipes.

Example 4

In a preferred embodiment, dual-band (Agema 880) infrared scanners are mounted on a positioning stand and co-aligned to image the same field of view at a distance of 26 inches from a test panel. Four flash lamps are positioned 16 inches from the panel and angled to provide uniform heating. The flash lamps are arranged in a square array (24 inches on a side). They are connected to the flash lamp control box and to the Agema computer. A firing button triggers the flash lamps and synchronizes the timing to start a data capture sequence 2.8 ms after the lamps fire. A typical sequence is 50 frames. Each frame has a duration of 160 ms. A frame consists of 4 interlaced fields, each with a duration of 40 ms. Thus, images are viewed on a display screen, recorded, and subsequently stored on the hard drive, resulting in a sequence of 200 consecutive (40 ms duration) DBIR images during the 8 seconds following a 4.2 ms heat flash.

Analysis consists of identifying and removing scanned areas with surface emissivity noise, and characterizing the time variations of surface temperature patterns which differ for structural sites with defects. These differences are used to quantify corrosion which produces thickness loss effects.

Example 5

A thermo plastic patch taken from an aircraft is placed in a freezer and then scanned. Areas of patch defects are observed as conducting heat at a different rate. The temperature changes between the inside and the outside so as the defective structure being evaluated equilibrates with room temperature, it acquires a different temperature from its surroundings. The bulk thermal properties of the defective site heats or cools at a different rate. The time sequence of the patch thermal images are then constructed into thermal inertia maps to facilitate analysis of the patch's defects.

Example 6

Sample panels known to be corroded were taken from an aged aircraft. Thickness measurements of the corroded surfaces of the samples were taken with a micrometer. An exterior side of the samples were flash heated. Images were obtained. Heat was observed to transfer faster through corroded areas (due to thickness loss) than non corroded areas. A correlation between percent thickness loss and above-ambient surface temperature rise at 0.4 seconds after the heat flash, averaged a 24±5% thickness loss per ° C. temperature rise.

Example 7

The thermal inertia of a fuselage was determined after scanning the fuselage lap splices of metallic panels joined together. Scanning was performed at a SWB and aLWB with two scanners. Each pixel contained in the images was converted into digital data and processed in order to form maps based on the inverse slope of the surface temperature versus inverse square root of time. The resulting thermal inertia maps allowed shallow skin defects within a lap splice to be detected at early times (<0.3s) and deeper skin defects within the lap splice to be detected at times of >0.4s.

In summary, information (each pixel) obtained from each image is converted into digital data and processed to derive thermal, temporal, emissivity, diffusivity, thermal inertia, spatial and spectral signatures (features) that may be used to uniquely characterize the structural defect type, size, shape, depth and location. Thermal inertia or effusivity is the $\sqrt{kpc}$ where k=conductivity, p=density and c=heat capacity of the base of the skin or outer layer of a structure. Diffusivity=k/(pc). Bulk thermal properties as used herein refers to one or more of the following elements: conductivity, density thermal inertia, diffusivity and specific heat.

While particular embodiments of this invention have been shown and described, it is readily understood that numerous modifications may be made to the method that would fall within the scope of the appended claims. For example, the wavelength ranges selected for scanning may be varied. Moreover, additional corrections to images (representing surface temperature and surface emissivity) may be made depending on the environment in which a particular structure is exposed to, i.e. pollution, dust, acid and other conditions.

What is claimed is:

1. A method for detecting a flow in a man-made structure, comprising the steps of:
 a) heating said structure with a heat source;
 b) scanning an area of said structure with at least two different wavelengths of radiation, wherein said scanning produces signals corresponding to surface temperature data and surface emissivity data of said structure at a plurality of points in time;
 c) obtaining a sequence of images from said scanning, wherein noise generated from clutter is eliminated from said sequence of images to form a corrected sequence of images; and
 d) determining from said sequence of corrected images whether a flaw exists in said structure.

2. The method of claim 1, wherein clutter is eliminated by separating surface temperature data from spatially-varying surface emissivity data to obtain apparent temperature values at scanned points of said structure.

3. The method of claim 2, wherein separating surface temperature data from spatially-varying surface emissivity data is achieved by using the following temperature ratio equation to obtain a temperature map:

$$[SWB/LWB=(\epsilon_5)(\epsilon_{10})*(T/T_0)^5]$$

$(T/T_{AV})^5=(S/S_{AV})/(L/L_{AV})$, where S is the short wavelength intensity., $S_{AV}$ is the average value of the pixels in S, L is the long wavelength intensity and $L_{AV}$ is the average value of the pixels in L.

4. The method of claim 3, wherein separating surface temperature data from spatially-varying surface emissivity data is further achieved by using the following emissivity ratio equation to obtain an emissivity ratio map:

$$[(LWB)^2/(SWB)=(\epsilon_{10})^2/(\epsilon_5)=\epsilon]$$
$$E-ratio=(L/L_{AV})^2/(S/S_{AV}).$$

5. The method of claim 4, wherein determining whether a flaw exists in said structure comprises comparing said temperature map with said emissivity-ratio map to observe heat flow anomalies generated by said flaw.

6. The method of claim 4 wherein a time sequence of said corrected temperature map is used to distinguish bulk thermal properties of said flaw from those of other areas of said structure where a flaw is nonexistant.

7. The method of claim 1, wherein said scanning comprises obtaining images during a predetermined interval of time.

8. The method of claim 7, wherein said images in said sequence are obtained at intervals of between 0.5 ms–100 ms, over a period of time ranging from 2 seconds to 8 minutes.

9. The method of claim 1, further comprising applying a dark coating onto said structure prior to said heating step when said structure is a metal.

10. The method of claim 1, wherein said flaw is located below the surface of said structure.

11. The method of claim 1, wherein said heating step occurs while said scanning is taking place.

12. The method of claim 1, wherein said scanning is performed with at least the same number of detectors as the number of scanned wavelengths.

13. The method of claim 1, wherein said scanning occurs for at least two different wavelengths comprising a long wavelength band ranging from 8–12 micrometers and a short wavelength band ranging from 3–5 micrometers.

14. The method of claim 1, wherein said structure is selected from aircraft, pipes, electronic components, bridges, decks, highways and landing strips.

15. The method of claim 1, wherein said structure is selected from infrastructure.

16. The method of claim 1, wherein said heat source is selected from a group consisting of a flashlamp and a laser.

17. The method of claim 1, wherein said clutter comprises tape, dirt, oil, grease, surface inhomogeneity, surface roughness or exposed metal or a combination thereof.

18. The method of claim 1, wherein said structure is analyzed using visual, photographic, x-ray, and acoustic sensor techniques to characterize said flaw.

19. The method of claim 1, wherein said image has a resolution within 0.2 degrees Celsius.

20. The method of claim 1, wherein said sequence of corrected images is used to detect a disbond in a lap joint.

21. The method of claim 1, wherein said sequence of corrected images is used to determine the size and depth of said flaw.

22. The method of claim 1, wherein said sequence of corrected images is used to detect delaminations in reinforced concrete structures.

23. A method for detecting a flaw in a structure, comprising the steps of:
   a) scanning an area of said structure with at least two different wavelengths of radiation;
   b) obtaining a sequence of images from said scanning, wherein noise generated from clutter associated with non-terrestrial surface emissivity from a man-made structure is eliminated from said sequence of images to form a sequence of corrected images; and
   c) determining from said sequence of corrected images whether a flaw exists in said structure.

24. The method of claim 23, wherein said structure comprises aircraft, electronic components, pipes, bridges, decks, highways and landing strips.

25. A method for determining the size of a flaw in a man-made structure, comprising:
   a) scanning an area of said structure using at least two different wavelength s of radiation;
   b) obtaining a sequence of images from said scanning;
   c) eliminating clutter associated with non-terrestrial surface emissivity from said sequence of images to form a sequence of corrected images; and
   d) determining the size, shape or depth or a combination thereof of said flaw from said corrected image in said structure.

26. The method of claim 25, wherein colors within said sequence of corrected images correspond to temperatures of said structure.

27. The method of claim 25, wherein said flaw is a corroded region of said structure.

* * * * *